United States Patent [19]

Smith et al.

[11] Patent Number: 5,424,046

[45] Date of Patent: Jun. 13, 1995

[54] METHOD AND APPARATUS FOR STEAM STERILIZATION

[76] Inventors: Benjamin G. Smith, 610 W. 25th St., Norfolk, Va. 23517; Kevin J. Shedd, 3561 Shannon Rd., Portsmouth, Va. 23703

[21] Appl. No.: 846,259

[22] Filed: Feb. 28, 1992

[51] Int. Cl.⁶ .......................... A61L 2/04; A61L 2/20
[52] U.S. Cl. .................................. 422/295; 422/297; 422/300; 422/307
[58] Field of Search ................. 422/26, 220, 27, 297, 422/33, 300, 40, 102, 104, 295, 32, 307, 294

[56] References Cited

U.S. PATENT DOCUMENTS

| 2,731,208 | 1/1956  | Dodd ........................... 422/26 |
| 3,027,244 | 3/1962  | Byrne et al. ................... 422/220 |
| 3,409,389 | 9/1968  | Bjork ............................ 422/26 |
| 3,672,009 | 6/1972  | Pike ............................ 422/208 |
| 3,983,260 | 9/1976  | Ford ............................ 422/26 |
| 4,337,223 | 6/1982  | Kaye ........................... 422/112 |
| 4,517,159 | 5/1985  | Karlson ......................... 422/20 |
| 4,522,015 | 6/1985  | Hildebolt ...................... 422/26 |
| 4,552,720 | 11/1985 | Baker et al. ................... 422/295 |
| 4,670,227 | 6/1987  | Smith .......................... 422/297 |
| 4,685,507 | 8/1987  | Schafer ........................ 422/295 |
| 4,759,909 | 7/1988  | Joslyn .......................... 422/26 |
| 4,933,149 | 6/1990  | Rhee et al. .................... 422/220 |
| 4,944,919 | 7/1990  | Powell ......................... 422/295 |
| 5,089,228 | 2/1992  | Meijer ........................ 422/38 X |
| 5,130,093 | 7/1992  | Wieczorek ..................... 422/26 |
| 5,217,688 | 6/1993  | Von Lersner ................... 422/26 |

FOREIGN PATENT DOCUMENTS

| 763148   | 7/1967  | Canada . |
| 776894   | 1/1968  | Canada . |
| 1600886  | 11/1970 | France . |
| 46-5779  | 2/1971  | Japan . |
| 28380    | 12/1913 | United Kingdom . |
| 197712   | 12/1977 | U.S.S.R. . |

Primary Examiner—Robert J. Warden
Assistant Examiner—Robert Carpenter
Attorney, Agent, or Firm—Stephen E. Clark

[57] ABSTRACT

An apparatus and method of sterilizing contaminated material by exposure to steam inside of substantially cylindrical, vertically oriented autoclave vessel. Contaminated material is shredded and bulk loaded from above autoclave vessel, directly into cylindrical wire mesh basket inside of vessel. Basket capacity exceeds 80% of volume of vessel. Path of thermal conductivity through contaminated material is reduced by inner sleeve along axis of basket. After completion of sterilization, top of autoclave vessel is opened, and basket containing sterilized material is removed by hoist positioned above the vessel.

9 Claims, 11 Drawing Sheets

METHOD AND APPARATUS FOR STEAM STERILIZATION

FIELD OF INVENTION

The present invention relates to processes for disinfecting and sterilizing. In particular, the present invention relates to a method and apparatus for sterilizing medical waste wherein a cylindrically shaped basket containing contaminated material is loaded into the top of a vertically oriented, substantially cylindrical autoclave, is sterilized by high temperature steam, and the sterilized waste is subsequently removed through the top of the autoclave.

BACKGROUND

Recently, interest has arisen over the disposal of medical waste, particularly as generated by hospitals, due to the public and environmental hazards that such waste may present.

A common method of treating medical waste involves sterilizing the waste materials in an autoclave system prior to disposing of the disinfected waste. In such prior systems, medical waste is typically first accumulated and pre-packaged in sealed plastic bags or in rectangular (or cubic) cardboard boxes.

The pre-packaged boxes or bags are then typically placed into a substantially rectangular-shaped, wheeled cart. When the cart becomes substantially filled with the pre-packaged boxes or bags, the cart is then rolled into an autoclave chamber. The autoclave chamber is essentially a high pressure steam vessel. Common high-capacity autoclaves are designed and constructed as cylinders having a horizontal axis, and are typically provided with an opening at one (or both) ends by which the wheeled carts carrying the pre-packaged boxes of medical waste can be rolled into the autoclave chamber.

With the cart and its contents enclosed within the autoclave chamber, saturated steam under pressure is typically introduced into the chamber for a period of time sufficient to sterilize the contents of the chamber. After the contents are sterilized, the chamber is vented, one (or both) of the ends of the cylinder is opened, and the carts with sterilized contents are rolled out of the autoclave for subsequent disposal of the sterilized waste.

Because of the increased interest and regulatory demands to treat medical waste, it has become desirable to increase the capacity, to reduce the cycle time, and to increase the energy efficiency of autoclaving systems.

A problem with using carts with a substantially rectangular cross-section inside of an autoclave chamber having a substantially circular cross-section is the inherent development of "dead space" (that is, unused volumes of air space within the autoclave chamber) which, although not used for any beneficial function, must be filled with steam during the autoclaving process. Such "dead space" significantly reduces the effective capacity, the thermodynamic efficiency, and the cycle time of prior autoclaving systems.

Another problem of prior horizontally oriented, cylindrical autoclaves is that wheeled carts containing medical waste must typically be rolled into the autoclave. Inherent in the use of wheeled carts in such prior systems is the development of "dead space" inside of the autoclave which results from providing a pathway and necessary clearance for the cart's wheels, and which additionally results from the wheels' lifting the cart a finite distance above the "floor" of the autoclave. As discussed previously, such "dead space" inside of the autoclave significantly reduces the effective capacity, the thermodynamic efficiency, and the cycle time of prior autoclaving systems.

Another problem of prior sterilization systems results from the common practice of pre-packaging the medical waste in plastic bags or in boxes, and subsequently placing those bags and boxes into rectangular carts. Because the individual items of medical waste are typically loosely disposed inside of the boxes, a significant percentage of the total volumetric capacity of the boxes is "dead space" (i.e. air), which must be heated during the autoclaving process. Additionally, because 100% of the total volumetric capacity of the carts available in prior autoclaving systems is not filled with the boxes (or bags) containing the pre-packaged medical waste material, a significant percentage of the total volumetric capacity of the carts is "dead space" (i.e. air), which must be heated during the autoclaving process. As discussed previously, such "dead space" significantly reduces the effective capacity and the thermodynamic efficiency of prior autoclaving systems.

Hospitals have for a long time had very small autoclaves, which were primarily used for sterilizing surgical instruments. As requirements for autoclaving of medical waste have increased, these small autoclaves have become adapted to handle the larger demands of hospital waste.

In an effort to increase the overall capacity of autoclaves, some prior devices are designed and constructed large enough to accommodate a plurality of carts containing pre-packaged containers of medical waste which can be hooked together to form a train of such carts. A problem of such systems is that in order to provide sufficient room for the cart-to-cart linking mechanism, "dead space" is developed between adjacent carts. As discussed above, such "dead space" significantly reduces the effective capacity and the thermodynamic efficiency of prior systems.

As a consequence of the pre-packaging of medical waste into sealed boxes, the irregular storing of these boxes in carts, the linking together of multiple carts, the provision of wheels upon which the carts roll, and the insertion of these carts of substantially rectangular cross-section into autoclaves of substantially circular cross-section, prior autoclaving systems typically are loaded to only 40% to 50% of total capacity (by volume) of the autoclave. That is, in prior autoclaving systems, typically 50% to 60% of the total capacity (by volume) of the autoclave is "dead space", as defined above.

In addition to reducing the energy efficiency of the autoclaving process, the prior method of linking carts together and pushing trains of sparsely filled carts into the horizontally oriented autoclave chambers results in a somewhat longer time for loading and unloading the autoclaves, and, hence, a longer total cycle time per unit mass of waste material.

In some prior autoclaving processes, a vacuum step is applied, usually at the beginning of the cycle, to remove air inside of the autoclave. This vacuum step provides a somewhat higher temperature when the steam enters the autoclave. In some prior devices a vacuum is also used at the back end of the autoclaving cycle, (i.e. after the waste material has been sterilized). This step primarily vents the excess steam and vacuum cools the autoclave and, therefore, saves some time in opening the autoclave unit.

In part because of the low density of the medical waste (or more specifically, because of the insulating pockets of air within the medical waste mass), thermal conductivity through the medical waste mass is relatively low. As a consequence of the relatively low thermal conductivity through the medical waste in prior autoclaving processes, the period of time necessary to heat (i.e. sterilize) the medical waste is relative long. Besides that achieved by the vacuum steps described above, prior autoclaving systems do not otherwise modify the contents of the autoclave in order to increase the thermal conductivity of the mass of medical waste. And in particular, prior autoclaving processes do not increase the water content of the medical waste mass, thereby reducing the matrix air within the mass itself, or increasing the density of the mass.

Another problem of prior autoclaving devices is that, because the steam is only applied to the outer surface of the pre-packaged, carted waste mass, it is sometimes difficult, energy inefficient, and time consuming to adequately heat the innermost elements of the waste mass.

OBJECTS

Accordingly, it is a primary object of the present invention to provide a method and apparatus for sterilizing medical waste by subjecting the said waste to high pressure steam inside of an autoclave chamber.

It is another object of the present invention to provide a method and apparatus of the character described wherein the autoclave chamber is filled to at least 65% (and upwards to 90%) by volume, thereby increasing the amount of waste material that can be processed per autoclave cycle.

It is another object of the present invention to provide a method and apparatus of the character described wherein the density of the waste material that is put into the autoclave unit is densified, thereby increasing the output of each autoclave cycle.

It is another object of the present invention to provide a method and apparatus of the character described in which the heat conductivity of the waste material is increased by reducing the volume of insulating air within the waste material itself.

It is another object of the present invention to provide a method and apparatus of the character described wherein the waste material is preheated prior to its being autoclaved, thereby reducing the cycle time and significantly increasing the thermal conductivity of the medical waste.

It is another object of the present invention to provide a method and apparatus of the character described in which the heat conductivity of the waste material is increased by replacing the matrix air by water vapor, water or a substance of higher heat conductivity.

It is another object of the present invention to provide a method and apparatus of the character described in which heat recovery from high pressure condensate provides improved thermal performance.

It is another object of the present invention to provide a method and apparatus of the character described in which the area of steam injection to the medical waste mass itself is significantly increased relative to prior autoclaving systems.

It is another object of the present invention to provide a method and apparatus of the character described in which the vacuum stages of prior autoclaving processes can be reduced or made unnecessary.

It is another object of the present invention to provide a method and apparatus of the character described whereby an autoclave may be quickly loaded and unloaded from above by baskets containing medical waste, and which baskets substantially fill the inside volume of the autoclave unit.

It is a further object of the present invention to provide a method and apparatus of the character described in which the thermal path from the outside surface(s) of the medical waste mass to the innermost elements of the medical waste mass is significantly reduced relative to that which exists in prior autoclaving apparatus. In particular, the longest such thermal path of the present invention is disclosed as being less than 22 per cent of the cross-sectional diameter of the medical waste mass.

It is another object of the present invention to provide a method and apparatus of the character described in which the ratio of the autoclave weight and the accessory weight (i.e. carts) to the weight of the contained waste is lower than that provided by prior autoclaving methods and apparatus.

These and further objects and advantages of the present invention will become apparent from a consideration of the drawings and ensuing description thereof.

DRAWINGS

DESCRIPTION

The disclosed invention is an autoclaving process and apparatus primarily adapted for sterilizing medical waste (generally designated as W in the figures). However, it will be appreciated that other non-medical waste materials may similarly be sterilized by employing the disclosed process and apparatus.

An autoclave (generally designated 1 in the figures) comprises a substantially cylindrically shaped pressure vessel 2. In operation, the axis of the vessel 2 is vertically oriented. An openable top hatch 3 is provided at the top of the vessel 2. In the preferred embodiment of the invention, top hatch 3 can be completely opened, by use of a hydraulic cylinder 4 or other common means, thereby exposing the entire cross-sectional area of the inside of the vessel 2 from above.

Figure 2:
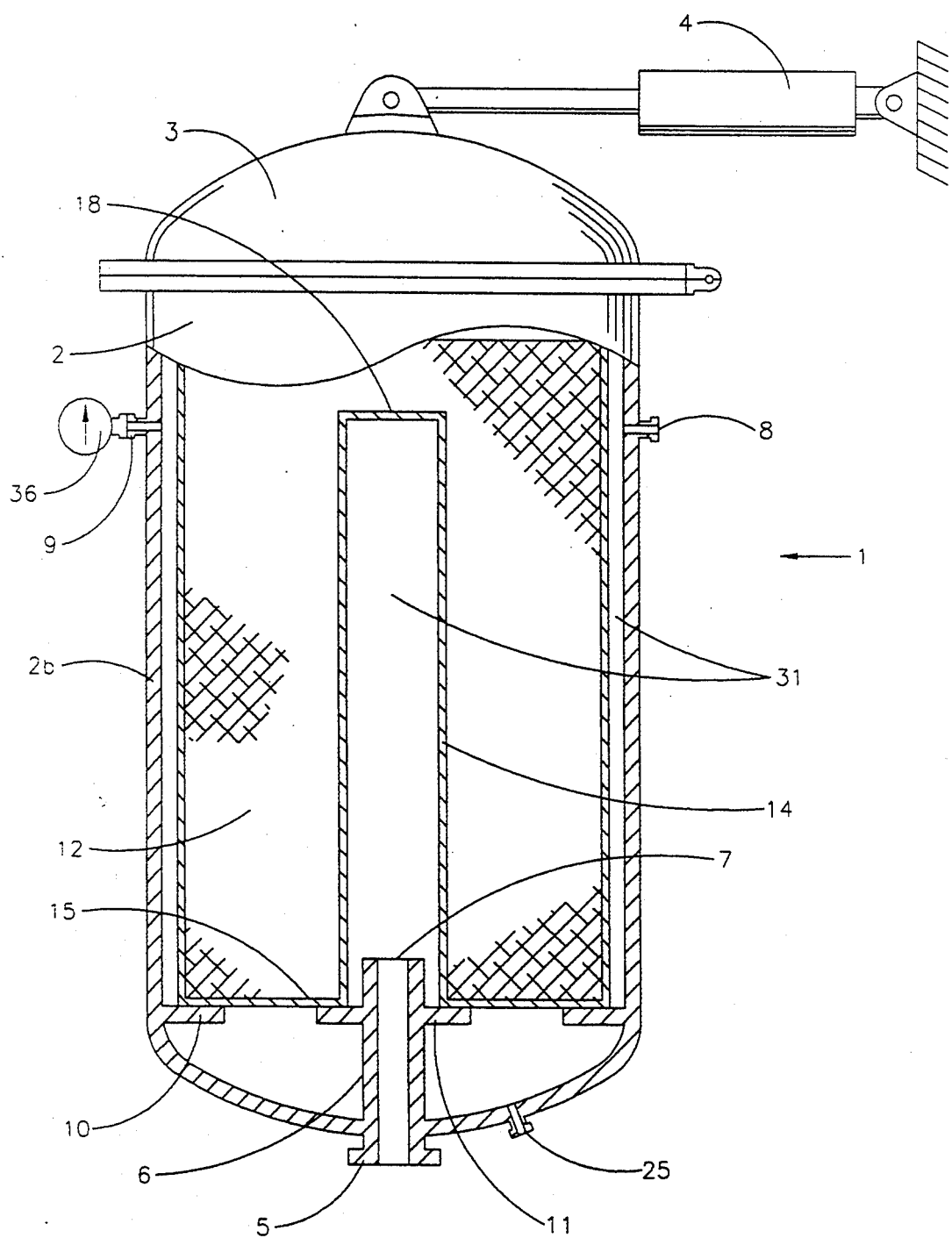
FIG. 2 is a medial cross-sectional view showing construction of the autoclave unit of the present invention.

A condensate drain 25 is located in the bottom of the vessel 2. A steam inlet bib 5, extending from a steam inlet conduit 6, is preferably located in the center of the bottom of the vessel 2, (as shown in FIG. 2), and directed along the axis of the vessel 2. On the interior of the vessel 2, a steam inlet orifice 7 in the steam inlet conduit 6 provides a means of ingress of steam into the vessel 2. A closeable steam vent orifice 8 is provided in the side wall of the vessel 2. Additional orifice(s) 9 may be provided in the side wall of the vessel 2 for purposes of installing temperature—or pressure-monitoring gauges 36, as shown in FIG. 2.

A basket mounting bracket 10 is attached to the inside of the vessel 2 near the bottom of the vessel. In the preferred embodiment of the invention a center basket support 11 is attached to the inlet conduit 6.

Figure 3:
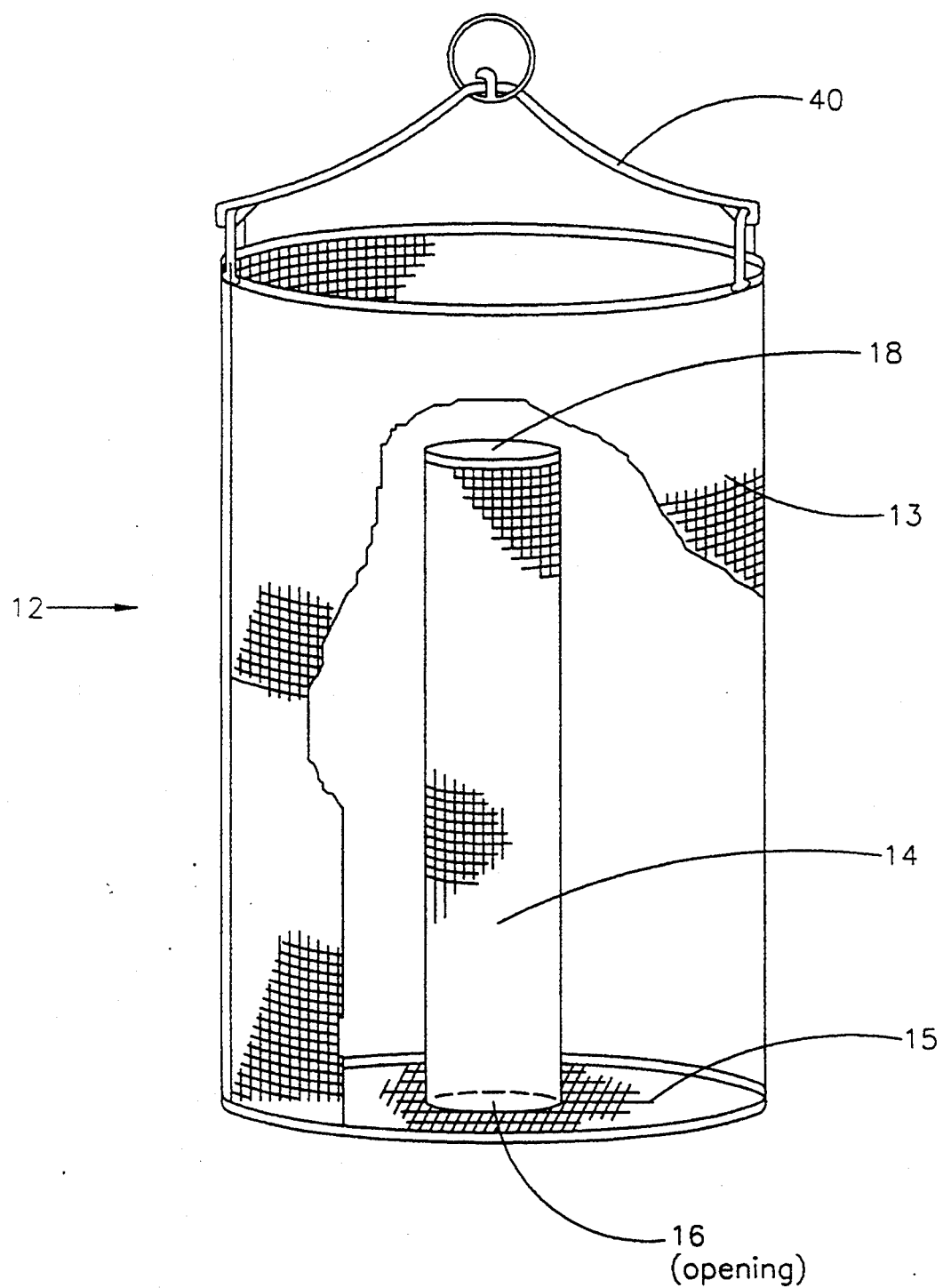
FIG. 3 is a perspective view showing construction of the wire basket used in the present invention.

A substantially cylindrically shaped basket, generally indicated 12 in the figures, is adapted to seat inside of the vessel 2, as shown in FIG. 2. Preferably a basket 12 having an overall length of 8'-0" and an outside diameter of 6'-0", is used inside of an autoclave 1 having a vessel sidewall 2b with a cylindrical height of approximately 8'-6" and an inside diameter of 6'-6". As shown in FIG. 3, the basket 12 comprises a cylindrical outside wall 13 and a cylindrical inner sleeve 14, each preferably constructed of a stiff wire open mesh having an opening area of between 60% and 75%. In the preferred embodiment of the invention the basket is constructed of 12 gauge, stainless steel wire mesh. One end (i.e. the bottom) of the outside wall 13 and one end (i.e. the bottom) of the inner sleeve 14 of the basket are each attached to a basket bottom 15. In the preferred embodiment of the invention, the bottom 15 of the basket is constructed of a stainless steel mesh, but it may alternatively be made of perforated or solid metal, as well as other suitable materials. An opening 16 is provided in the center of the basket bottom 15 to allow the steam inlet conduit 6 to pass through the basket bottom 15 and into the inner sleeve 14 when the basket 12 is inserted into an autoclave 1, as shown in FIG. 2.

The basket's inner sleeve 14, which preferably has a diameter of approximately 12 inches, extends from the basket bottom 15 along the axis of the basket 12 and terminates inside of the outside wall 13. A sleeve cap 18 is attached to the top end of the inner sleeve 14.

As shown in FIG. 2, when the basket 12 is inserted inside of the autoclave vessel 2, the basket bottom 15 rests on the basket mounting bracket 10 and the center basket support 11. The basket 12 is open towards the top end of the autoclave vessel 2 so that the basket may be filled from above. In operation, the sleeve cap 18 prevents waste material from falling into the inside of the inner sleeve 14 when waste material is dropped into the basket from above.

Figure 1:
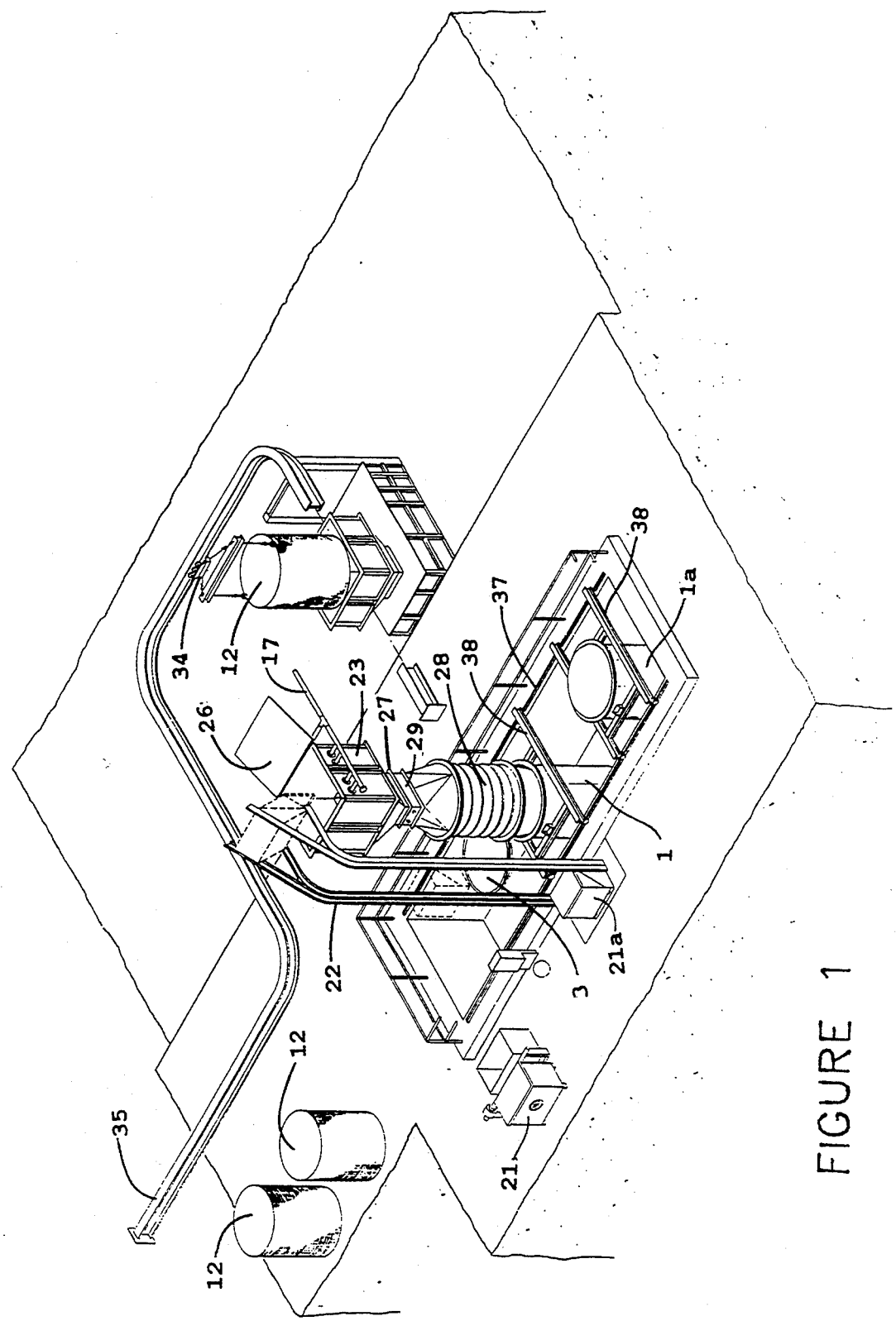
FIG. 1 is a perspective view showing the present invention.

Referring to FIG. 1: An autoclave positioning carriage 38 which rides on an autoclave positioning rail 37 provides a means for selectively positioning the autoclave units 1 either underneath a feed hopper 23 (for loading with waste material), or away from the feed hopper 23 (for unloading waste material). A hoist 34 which travels on an overhead rail 35 is provided to selectively load and unload baskets 12 into and out of autoclaves 1 from above.

OPERATION

Figure 8:
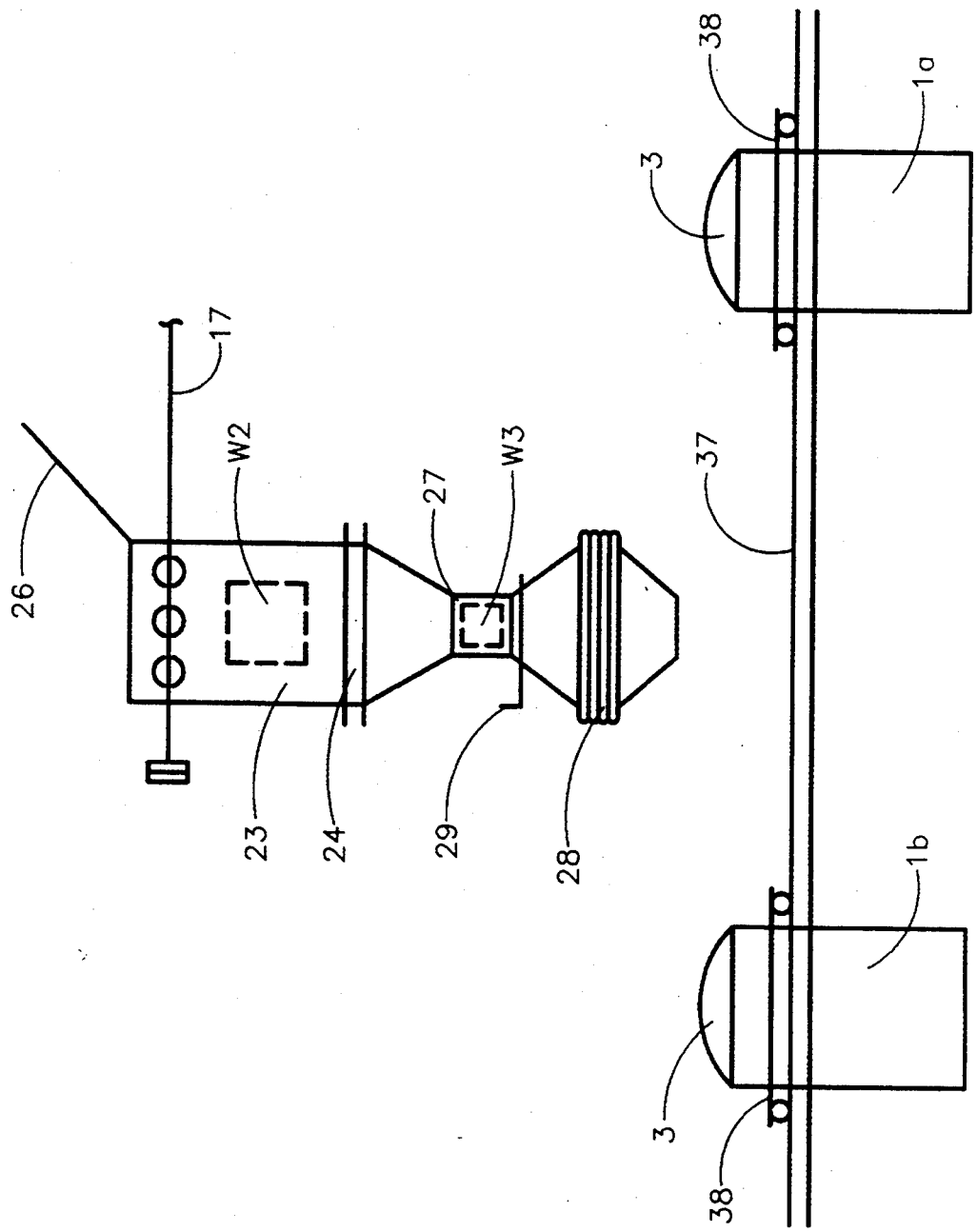
FIG. 8 is a side elevation of the present invention showing an open feed hopper ready for loading.

Referring to FIG. 1 and FIG. 8: The process begins by loading pre-package, sealed boxes or bags of medical waste W1 into wheeled storage carts 21. A skip hoist 22 then lifts a cart 21a over the top of an open feed hopper 23, and dumps the medical waste contents W1 of the cart 21a into the feed hopper 23. The batch weight of the medical waste W2 inside of the feed hopper 23 is monitored by a hopper strain gauge weighing unit 24. In order to reduce emissions from the feed hopper 23, a negative pressure is maintained in the hopper 23 at all times during operation. Negative pressure is provided to the feed hopper by a vacuum air piping system 17. Emissions from the feed hopper 23 may additionally be reduced by closing a feed hopper door 26 on the top of the hopper 23 when waste is not being dumped into the hopper 23.

Figure 9:
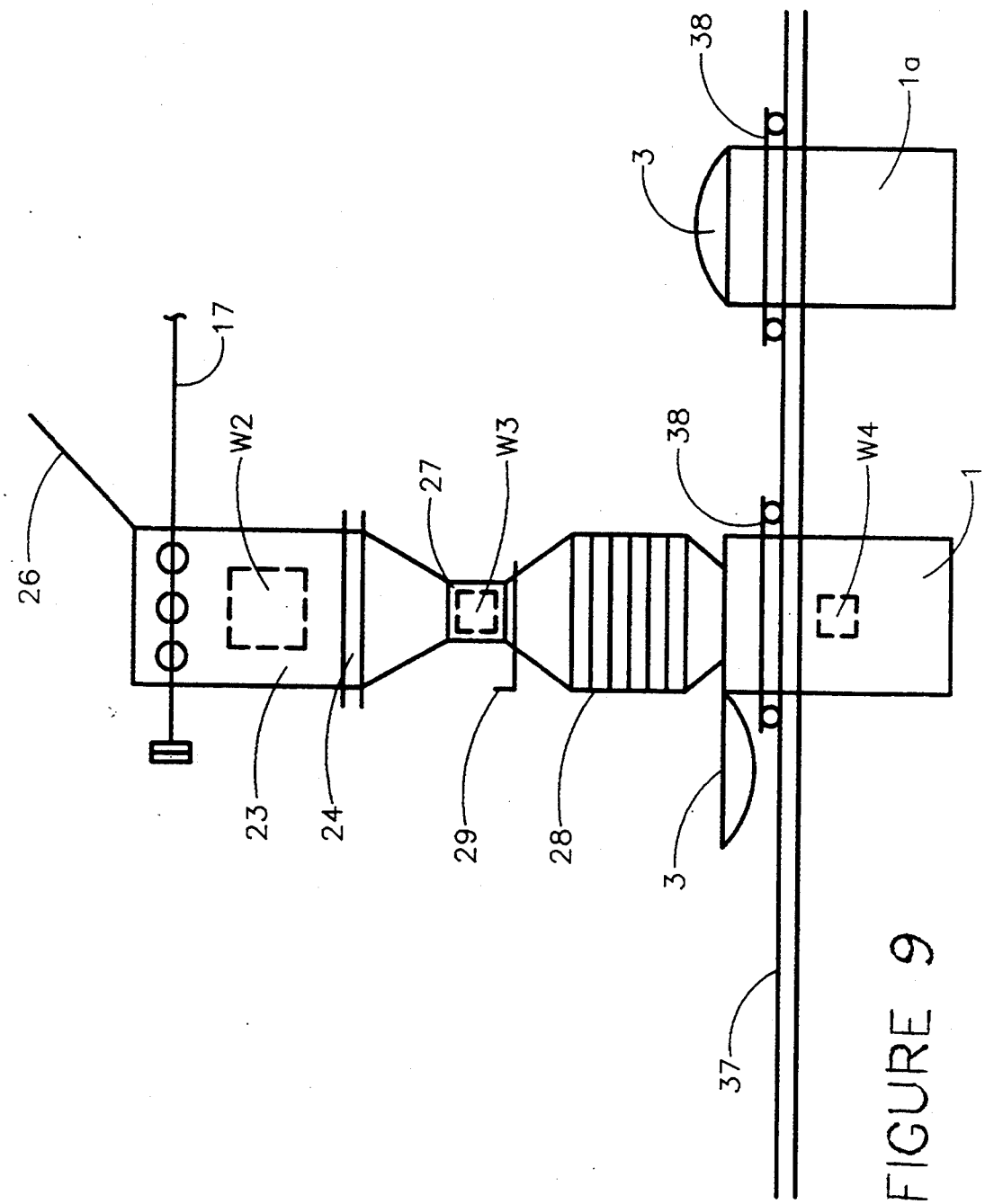
FIG. 9 is a side elevation of the present invention showing an autoclave unit positioned beneath a shredder.

Referring to FIG. 1 and FIG. 9: A shredder 27 is attached to the underside of the feed hopper 23. With the feed hopper door 26 closed, the pre-packaged medical waste W2 passes from the feed hopper 23 to the shredder 27 (by gravity), whereupon the shredder 27 shreds the waste material W3 (as well as the bags or boxes in which it may be contained) into small fragments. A telescoping spout 28 extends downward from the bottom of the shredder 27. While the top of the telescoping spout 28 is fixed to the bottom of the shredder 27, the bottom of the telescoping spout 28 can be raised and lowered as necessary. A gate 29 is provided at the top of the spout to open and close the passage between the shredder 27 and the spout 28. With the bottom of the telescoping spout 28 initially in the raised position (as shown in FIG. 8), an opened autoclave 1 containing an empty basket 12 is hydraulically moved into position under the shredder 27 and the spout 28. When the autoclave 1 is in position beneath the shredder 27, the bottom of the telescoping spout 28 is lowered until it engages and seals the circumference of the top of the autoclave 1, as shown in FIG. 9. The gate 29 is then opened, and the pre-weighed, shredded waste W3 is discharged from the shredder 27, through the telescoping spout 28, and into the basket 12 which is inside of the autoclave 1. The autoclave 1 is preferably filled to approximately 85% of its total volumetric capacity with the shredded waste material W4.

Once the autoclave 1 is full of the medical waste W4, the gate 29 is closed, and the telescoping spout 28 is disinfected and retracted (i.e. raised). The hatch 3 is then closed, thereby sealing the autoclave 1 for subsequent steam sterilization of the medical waste W4 that is inside of the autoclave. The sealed autoclave 1a may be hydraulically repositioned away from beneath the shredder 27, thereby freeing up the telescoping spout 28 (for filling of any additional autoclave units 1).

Figure 7:
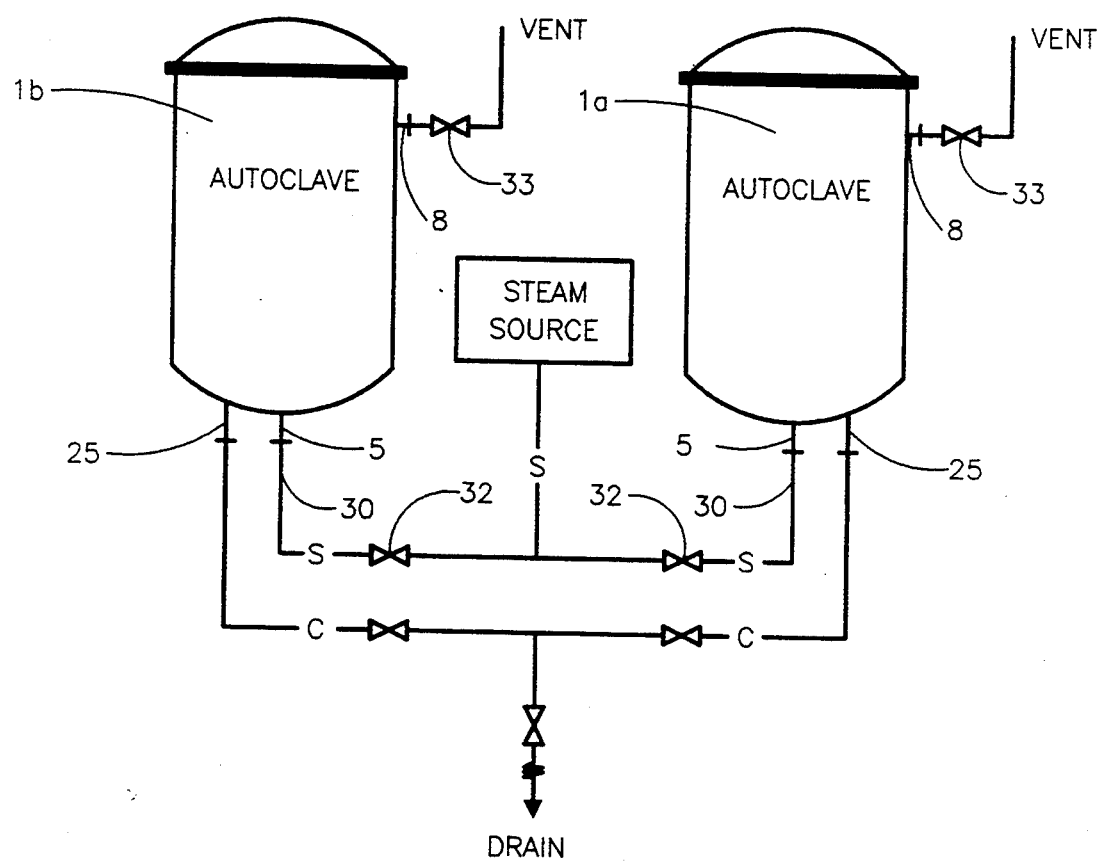
FIG. 7 is a schematic diagram showing the piping system of the present invention comprising dual autoclaves.

Referring to FIG. 2 and FIG. 7: Saturated steam, (preferably at 80 psig) is then introduced into the repositioned, sealed autoclave 1a via steam supply piping 30 connected to the autoclave's steam inlet bit 5. The saturated steam initially fills the air spaces 31 within the autoclave vessel 2 which are not occupied by the basket 12 or its waste material W4 contents. More specifically, the steam fills the air space below the bottom of the basket 15; the air space above the basket 12; between the basket's outside wall 13 and the autoclave vessel's sidewall 2b; and within the basket's inner sleeve 14. As discussed previously above, the total volume of the air spaces 31 is preferably less than 15% of the total capacity of the autoclave vessel 2. The elevated temperature of the steam located between the outside wall 13 of the basket and the sidewall 2b of the autoclave vessel causes the medical waste material W4 contained in the basket 12 to heat up from the outside wall 13 of the basket towards its center. The elevated temperature of the steam located inside of the basket's inner sleeve 14 causes the medical waste material W4 contained in the basket 12 to heat up outwardly from the center of the basket 12. The heat continues to conduct through the medical waste material W4 until all of the waste material inside of the autoclave 1 is heated to a sterilization temperature of at least 240 degrees Fahrenheit. In the preferred embodiment of the invention, the medical waste W4 is heated for a period of approximately one-half hour, for a total cycle time of approximately 45 minutes.

In the preferred embodiment of the invention, the inside diameter of the autoclave vessel 2 is 6'-6"; the outside diameter of the basket 12 is 6'-0"; and the diameter of the basket's inner sleeve 14 is 12". It will be appreciated by those skilled in the art that, in the device thus disclosed, the longest thermal path through the medical waste mass W4 from an air space 31 which is directly heated by saturated steam is never more than $15\frac{1}{2}$". Although the disclosed basket 12 can contain 96% of the volume of medical waste W4 of a similarly sized basket which has no inner sleeve, the maximum thermal path ($15\frac{1}{2}$") through the waste material W4 in the disclosed basket 12 is only 43% of the maximum thermal path (36") through a similarly sized basket which has no inner sleeve. It will be appreciated by those skilled in the art that by reducing the length of the thermal path through the medical waste W4, the total time and the total amount of steam consumption necessary to bring the entire mass of the medical waste W4 up to sterilization temperature is reduced.

It will also be appreciated by those skilled in the art that the disclosed apparatus (in particular, a cylindrical basket inside of a cylindrical autoclave vessel) has approximately 1.5 times the volumetric capacity of optimally designed baskets having square cross-sections which may be used inside of similarly sized cylindrical autoclave vessels, (such as is typically employed by the prior art).

Figure 10:
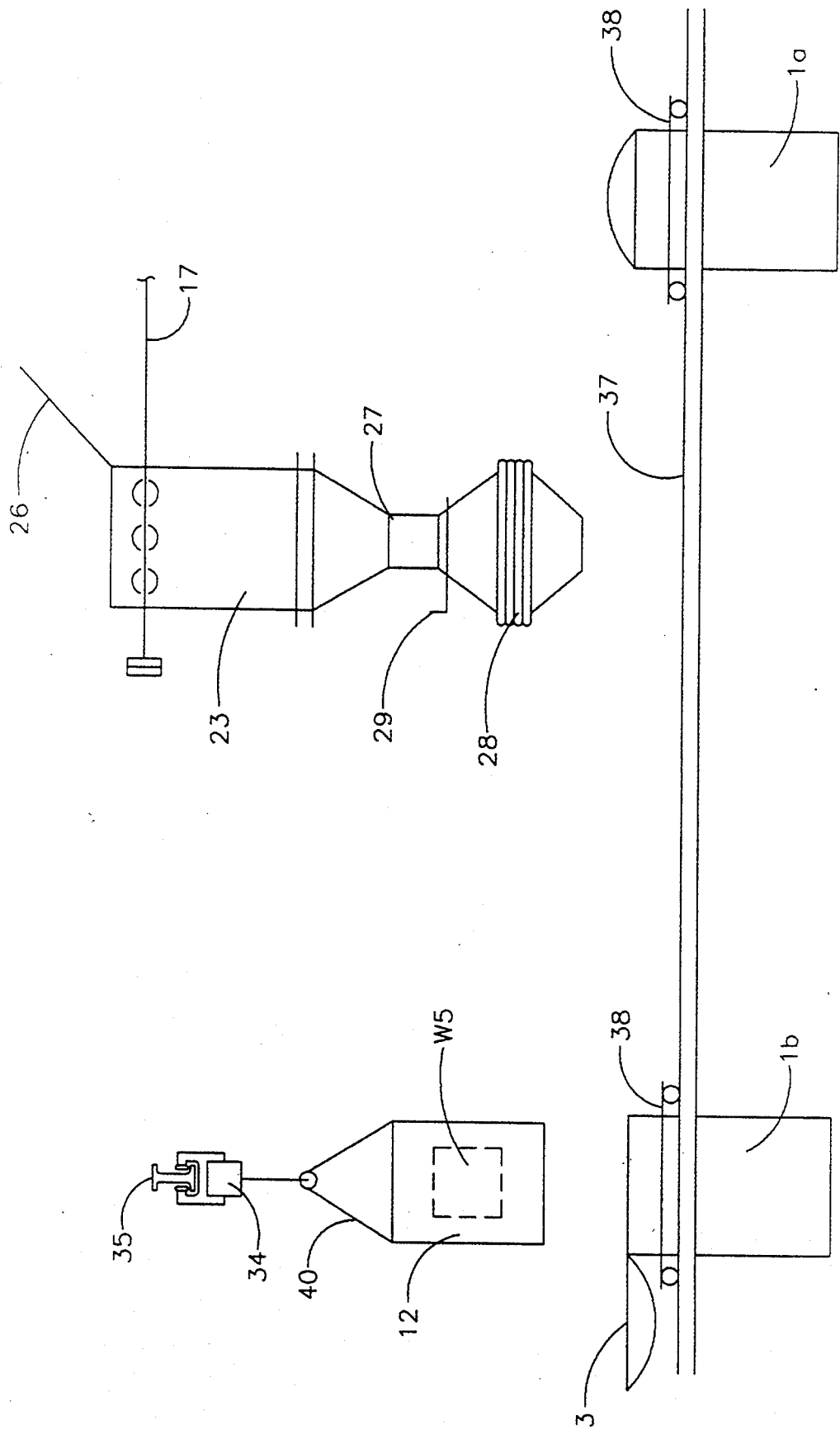
FIG. 10 is a side elevation of the present invention showing a suspended basket being removed from an open autoclave unit.
Figure 11:
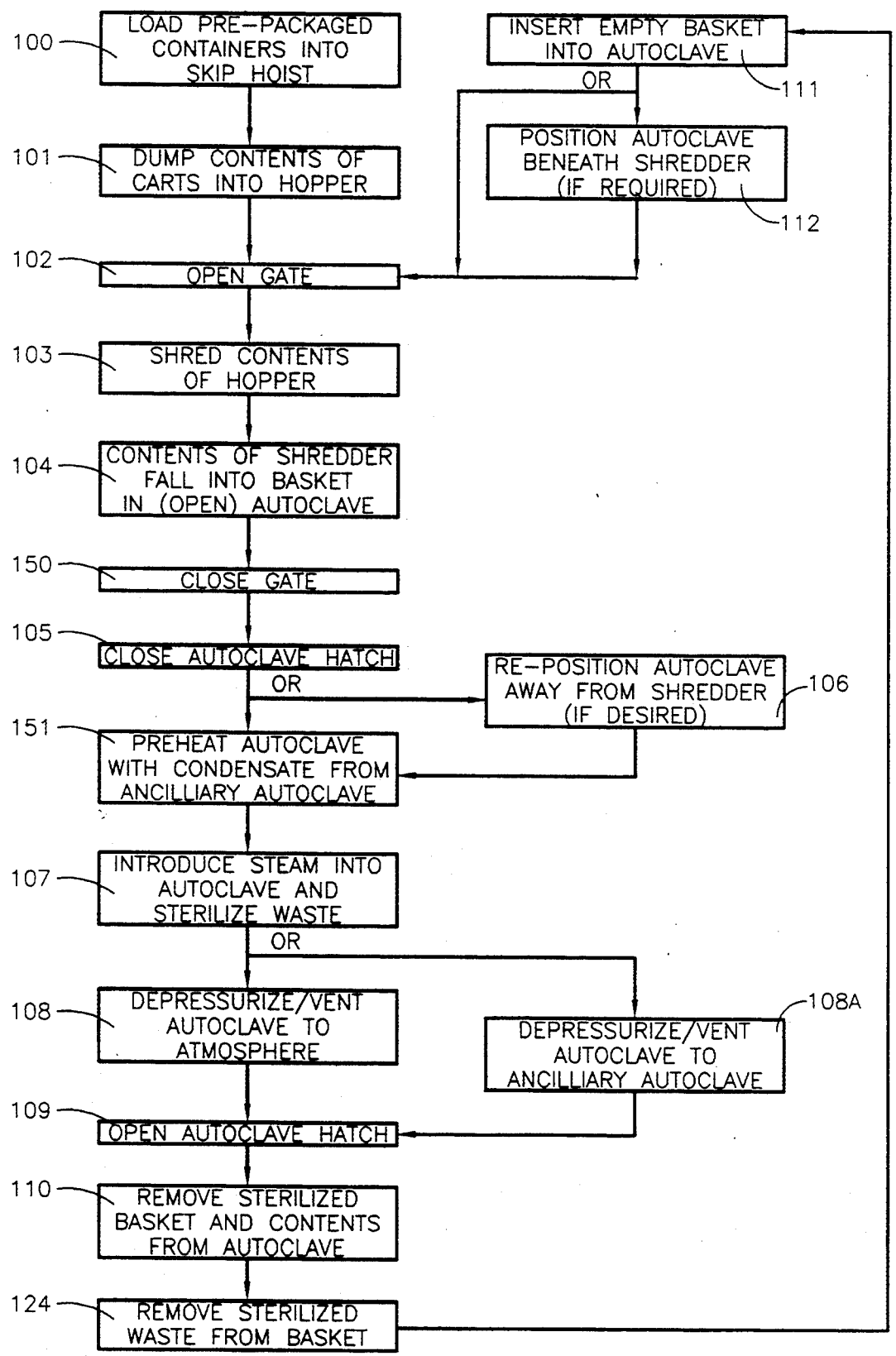
FIG. 11 is a flow diagram showing a modification of the invention.

Referring to FIG. 7 and FIG. 10: After the contents of the autoclave 1 have been sterilized, the steam inlet valve 32 is closed, thereby cutting off the supply of steam to the autoclave unit 1b. A steam vent valves 33 is then opened, thereby relieving the pressure and reducing the temperature inside of the autoclave 1b. At about the same time that autoclave unit 1b is being shut off and about to be depressurized, a second autoclave unit 1a is charged or being charged. Pressurized autoclave unit 1b may then discharge its flashing condensate into the second autoclave unit 1a, preheating and improving its thermal conductivity. The hatch 3 of the depressurized autoclave can then be opened. A hoist 34, which rides on an overhead rail 35, is positioned over the opened autoclave and lifts the basket 12 of sterilized medical waste material W5 out of the autoclave 1b. A bridle 40 is provided at the top end of the basket 12 to facilitate lifting of the basket. The suspended basket 12 holding the sterilized medical waste material W5 can then be conveyed (via the overhead rail 35) for subsequent compacting and disposal of the waste material W5.

Condensate which is generated as the saturated steam cools inside of the autoclave 1 collects at the bottom of the vessel 2, and may subsequently be drained through the condensate drain 25.

It will be appreciated by those skilled in the art that, because the disclosed autoclave 1 can be loaded and unloaded from above, the basket 12 can be constructed as disclosed to conform to the shape and size of the inside of the autoclave vessel 2 in which it is being inserted. This allows for a more efficient use of the volumetric capacity of the autoclave 1 units than was possible in prior autoclaving processes, as well as a quicker and more efficient method of loading and unloading the autoclave.

SUMMARY OF THE PREFERRED PROCESS

Figure 4:
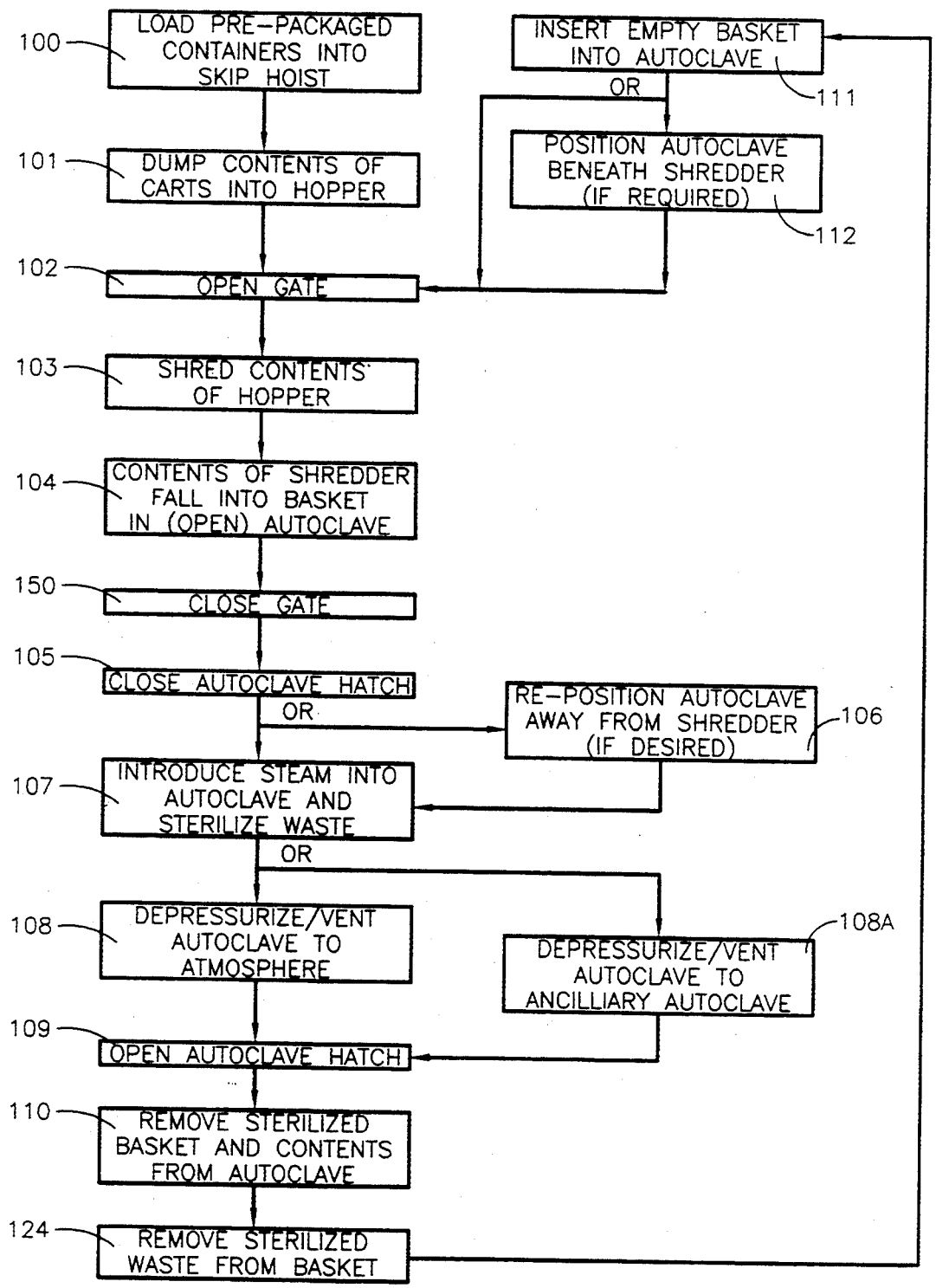
FIG. 4 is a flow diagram of the preferred embodiment of the process of the present invention.
Figure 5:
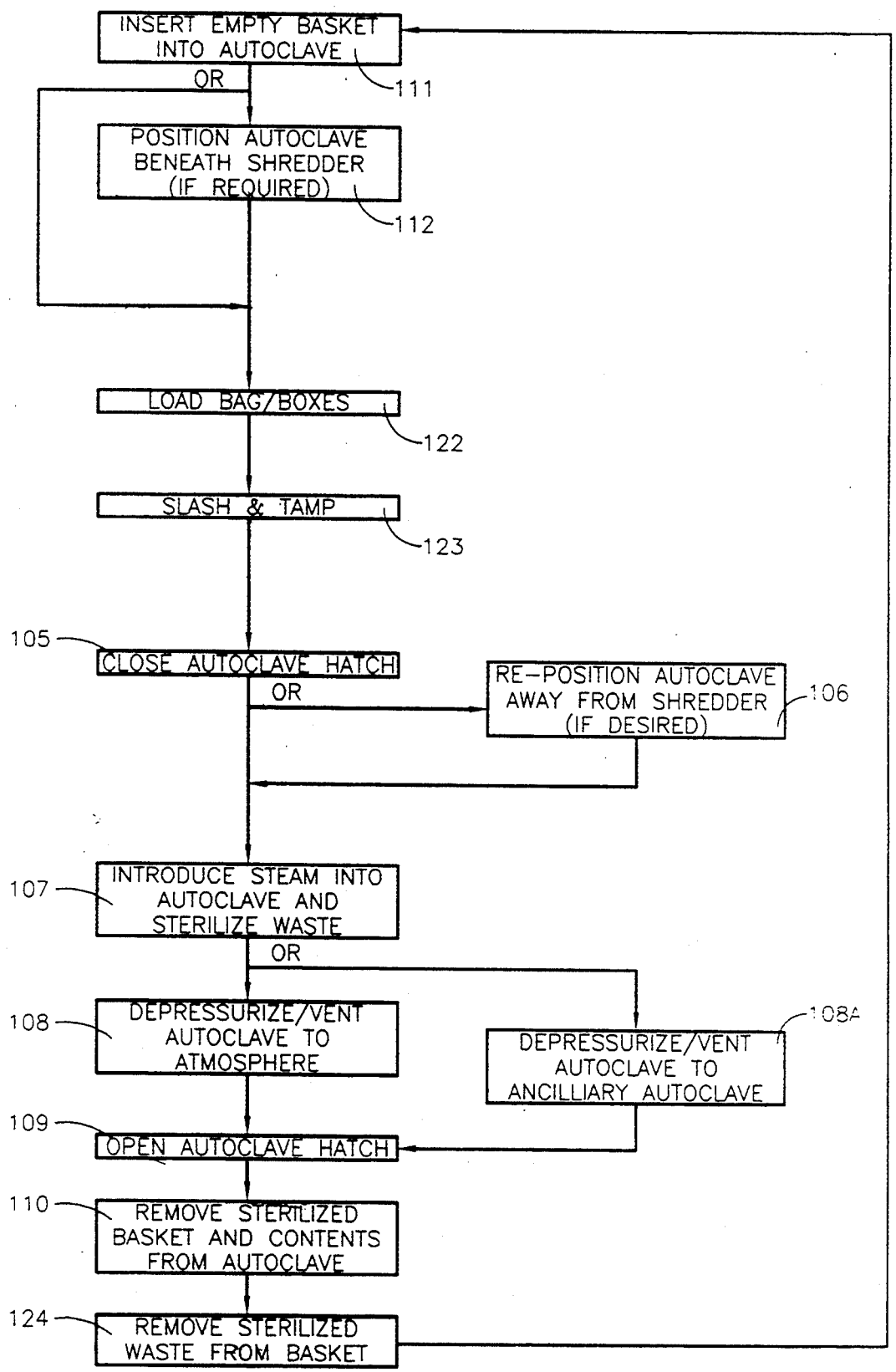
FIG. 5 is a flow diagram of a modified embodiment of the process of the present invention.
Figure 6:
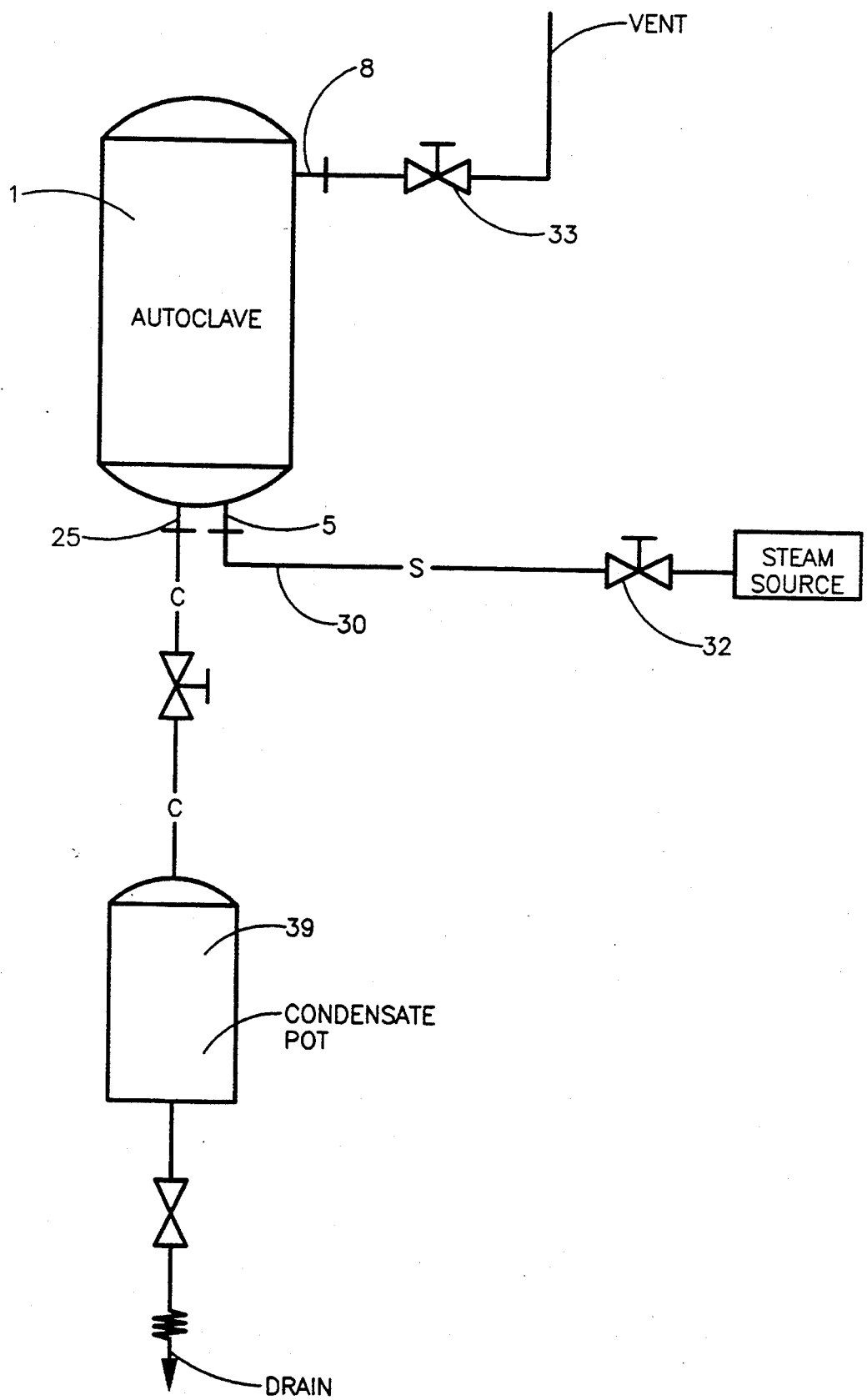
FIG. 6 is a schematic diagram showing the piping system of the present invention having a single autoclave vessel.

Referring to FIG. 4: The above disclosed process is summarized as follows:

The pre-packaged bags and boxes of medical waste are loaded into wheeled carts (100). The contents of the wheeled carts are dumped into the closeable feed hopper (101) via a skip hoist. An empty basket is inserted into an autoclave vessel (111), which is subsequently positioned beneath the shredder (112). The gate opens (102), allowing the contents of the shredder to fall into a basket inside of the autoclave vessel (104). The contents of the feed hopper pass to the shredder, whereupon the medical waste is shredded (103). After the basket is substantially full, the hatch on the autoclave vessel is closed (105), and the autoclave may be repositioned from beneath the shredder (106). Steam is then introduced into the autoclave, which sterilizes the contents of the autoclave vessel (107). After the contents of the autoclave have been sterilized (107), the autoclave vessel is vented (108), and the hatch may be opened (109). The sterilized basket and its contents are then removed from the opened autoclave vessel (110). The sterilized contents of the basket may then be safely removed from the basket (124), whereupon the empty basket is then available to be inserted into an empty autoclave (111) for reuse.

As discussed previously above, it is possible to more completely fill the autoclave 1 of the present invention with medical waste W than is practical with prior autoclaving devices. Accordingly, prior autoclaving processes have a greater ratio of autoclave weight and accessory weight (carts, etc.) to the weight of the contained waste, than does the present invention. Since the process is cyclical, (i.e., heats up and then cools down to unload and reload the autoclave 1), the heat dissipated to the autoclave vessel 2 and extraneous materials (i.e. basket 12, etc.) during the process represents a heat loss whose value can be represented as a percentage of the total heat requirement for the autoclaving process.

Table 2 shows calculations of the heat requirements, per pound of waste material, for the preferred embodiment of the invention. Table 3 shows calculations of the typical heat requirements, per pound of waste material, for a comparable prior art autoclaves. Table 1 shows the assumed values for constants used in the calculations shown in both Table 2 and Table 3.

Referring to Table 3: Calculations indicate that approximately 31% of the heat in comparable sized conventional prior autoclaving systems is used to sterilize (i.e. heat) the contained waste, while the remaining 69% of the heat is lost. The largest single heat loss in prior devices is typically the heat spent heating the autoclave unit itself (rather than heating, for example, the waste material contained inside of the autoclave unit).

Referring to Table 2: In the present invention, where the ratio of the weight of the waste W to the weight of the autoclave 1 is much higher than in comparably sized prior devices, nearly 50% of the total heat requirement is applied directly to the sterilization process (i.e. heating the contained waste W).

In the present invention not only is the ratio of the weight of the waste W to that of the autoclave 1 higher than for prior processes, but the ratio of the volume of the waste W to that of the autoclave 1 is also higher than for prior processes. At the end of the sterilization, all the steam in the unoccupied space 31 within the autoclave 1 is vented (108). Because of the relatively smaller amount of unoccupied volume 31 within the autoclave 1 in the present invention, a smaller proportion of the heat is wasted heating unoccupied spaces in the present invention.

Thus, it can be seen that the disclosed invention is capable of sterilizing the contained waste with more thermodynamic efficiency (and therefore less expensively) than could be done with prior autoclaving processes.

TABLE 1

Factors and Constants Used:

| | |
|---|---|
| Waste: | C = 0.40 BTU/lb-F |
| | Temperature In: 50 deg. F. |
| | Temperature Final: 280 deg. F. |
| | Pressure, final: 80 psig |
| | Waste Density: 6 lb/cu. ft. |
| Steam: | 80 psig saturated, $h_s$ = 891.5 |
| | Temperature = 324 deg F. |
| | v = 4.65 cu. ft./lb |
| | $h_f$ = 294.7  $h_T$ = 1186 |
| Autoclave: | Vent volume = [0.2/0.8] / [6 lb/cu ft] = 0.0416 cu ft |
| | Cool down to 200 deg F. |
| | Weight: 6.51 × 8 ft = 5209 |
| | Spefic Heat: 0.11 BTU/lb |

TABLE 2

PREFERRED EMBODIMENT

Weight of Autoclave:

6.5′ dia × 8′ (Single Door)
Cylinderical Area

| | |
|---|---|
| pi D L = pi × 6.5 × 8 = | 163 sq ft |
| Ends (assume spheric) | |
| 4 pi D D/4 = | 133 sq ft |
| Add 15% = | 44 sq ft |
| | 341 sq 4t |

3/8″ plate @ 15.3 lb/cu ft
Autoclave Weight (preferred embodiment):

341 × 15.3 = 5,209 lb
Total Volume of Waste in Present Invention:

Volume of Basket =
= pi D D L/4 − pi D D (L − 1)
= pi/4 × (252 − 1.5)
= 196.7 cu ft
Total weight capacity of Basket
(Preferred Embodiment):

196.7 cu ft @ 6 lb/cu ft = 1180 lb
Calculation of Heat Requirement per Pound of Waste:

| | | |
|---|---|---|
| a) | To Waste: 1 × 0.4 × (280 − 50) = | 92.0 BTU |
| b) | To Vent: 0.0416 cu ft/[4.65 cu ft/lb] × 1186 BTU/lb = | 10.6 BTU |
| c) | To Autoclave: Wt Autoclave/Wt Waste 5209/1180 = 4.414 4.414 × 0.11 × [280 − 200] = | 38.8 BTU |
| d) | Radiation Loss @ 2% = | 3 BTU |
| e) | To Condensate: Weight Condensate Heat a, b, & d | |

TABLE 2-continued

PREFERRED EMBODIMENT

| | |
|---|---|
| (92 + 39 + 3)/891.5 = 0.1503 lb Heat = 0.1503 × 294.7 = | 44 BTU |
| TOTAL HEAT REQUIREMENT (per lb of Waste) | 188.5 BTU |
| TOTAL STEAM REQUIREMENT: [188.5 BTU/lb] / 1186 BTU/lb = 0.159 lb steam per lb of waste | |

TABLE 3

PRIOR ART AUTOCLAVE (Typical Example)

Weight of Typical Prior Art Autoclave:

8′ dia × 30′ long (Double Doors)
¼″ thick steel plate
Cylinder Section:

| | |
|---|---|
| pi D L = pi × 8 × 30 = | 754.0 sq ft |
| Spherical Heads: | |
| pi D D = | 201.1 sq ft |
| | 955.1 sq ft |
| Add 15% = | 143.3 sq ft |
| | 1098.4 sq ft |

¼″ plate @ 20.4 lb/cu ft

| | |
|---|---|
| Wt (Autoclave) = 1098.4 × 20.4 = | 22407 lb |
| Wt (Guides & Rails) = | 1000 lb |
| Wt (Carts) = | 3000 lb |
| Total Weight | 25407 lb |

Total Internal Volume (less heads):

| | |
|---|---|
| Vol = pi D D L/4 = pi × 8 × 8 × 30/ 4 = | 1508 cu ft |
| Waste Volume @ 45% = | 697 cu ft |
| Waste Weight @ 4.5 lb/cu ft = | 3053 lb |

Weight per pound of Waste:

| | |
|---|---|
| 25407/3053 = | 8.322 lb/lb |

Unoccupied vol per lb waste:

| | |
|---|---|
| (1508 − 697)/3053 = | 0.2715 cu ft |

Calculation of Heat Requirements Per Pound of Waste Heat:

| | | |
|---|---|---|
| a) | To Waste: 1 × 0.4 × (280 − 50) = | 92.0 BTU |
| b) | To Vent: 0.2715 cu ft/[4.65 cu ft/lb] × 1186 BTU/lb = | 69.2 BTU |
| c) | To Autoclave: Wt Autoclave/Wt Waste 8.322 × 0.11 × [280 − 200] = | 73.2 BTU |
| d) | Radiation Loss @ 2% = | 4.7 BTU |
| e) | To Condensate: Weight Condensate Heat a, b, & d (9 + 73.2 + 4.7)/891.5 × 294.7 = | 56.2 BTU |
| TOTAL HEAT REQUIREMENT (per lb of Waste) | | 295.3 BTU |
| TOTAL STEAM REQUIREMENT: [295.3 BTU/lb] / 1186 BTU/lb = 0.249 lb steam per lb of waste | | |

It may generally be stated, within certain limits, that the rate of heat transfer is approximately proportional to the temperature difference between the heating fluid (steam) and the waste W. Most of the heat from the steam is released at its saturated temperature. For pure steam at one atmosphere, this would be 212 degrees F; for steam in a fifty-fifty mixture with air, this would be only 177 degrees F. Since the process of this invention more completely fills the volume of the autoclave 1, and does so in a more dense manner than is achieved in prior devices, the air contained in the autoclave 1 and its diluent effect are each much less than are provided by prior autoclaving processes.

A significant proportion of the total heat in the steam is discharged as condensate. If the condensate is discharged continuously, about 10% of the condensate heat is saved over discharging at the end of the cycle. However, it has been found that the bulk loaded vertical autoclave 1 of the present invention provides a particularly convenient opportunity for preheating while loading. In the preferred embodiment of the invention, a pair of autoclaves 1 are interconnected with a parallel piping system as generally shown in FIG. 7. When two or more autoclaves 1 are used in parallel, as shown in FIG. 7, after the waste W in one autoclave 1a has be sterilized as described above, the condensate drain 25 can be opened, allowing the condensate to drain out of the first autoclave 1a. The condensate may then be passed to the second autoclave 1b.

A schematic diagram showing the piping system of a modified embodiment of the invention is shown in FIG. 7. A condensate pot 39 is connected to the condensate drain 25 of the autoclave 1. The use of a condensate pot 39, allows the storage and re-use of high pressure condensate in subsequent autoclaving cycles. This feature, (preheating of waste), is not a necessary part of the present invention, but it is an economical accessory that fits more easily into this process than prior autoclaving processes. Steam savings of approximately 20% can be realized by preheating with high pressure condensate in the disclosed manner.

The effect of the moisture content of the medical waste is two fold. First, since the heat capacity of most solid wastes are about 0.30 BTU/lb-F whereas liquid water is three times greater; the steam required for a moist waste is greater than for the same weight of dry waste. Second, for moisture uniformly spread throughout the waste, the heat conductivity is significantly improved, especially at moderately high temperatures. This may be explained by realizing that a waste is like an insulation blanket, that the insulation characteristic is due to relatively immobile air, and that displacement of the air by lower molecular weight water vapor increases the conductivity.

By adding condensate to the autoclave 1b, it is desirable to increase the moisture content throughout the waste W to a more uniform level, while maintaining an overall moisture content of no more than 5-10%. In practice, this typically can be achieved by increasing the moisture content of the waste W by about 1-3%. Use of recycled high pressure condensate, as described above, effectively increases the conductivity without increasing the thermal load.

It can be appreciated that, because the disclosed apparatus, and in particular the basket 12, is adapted to the bulk loaded, it is not only possible to more completely occupy the autoclave 1 volume (as discussed previously, above), but the waste W may be easily densified during the loading process. Densification is desirable not only because more waste W may be sterilized within a relatively smaller volume, but because densified waste will more rapidly and more efficiently conduct heat (than would less dense waste). In the present invention, densification of the waste W can be achieved during loading by the choice of packaging of the waste, the method of loading, disintegration and maximum size of the waste structures during shredding. In addition, the waste W contained inside of the bulk loaded autoclave 1 may be further densified by tamping or by vibration-induced settling.

While the above description contains many specificities, these should not be construed as limitations on the scope of the invention, but rather as an exemplification of one preferred embodiment thereof. Many other variations are possible, for example:

The basket 12 can be supported inside of the autoclave 1 by brackets mounted either the sidewall 2b or the bottom 2a of the autoclave, or it may be constructed to rest directly against the bottom 2a of the autoclave vessel;

The steam inlet conduit may enter the autoclave from the side or the bottom of the autoclave vessel;

The steam inlet orifice 7 may be located at a positions other than inside of the basket's inner sleeve, and multiple steam inlet orifices may be provided inside of a single autoclave;

The basket may be constructed various materials, and may be perforated rather than mesh;

The waste material which is to be sterilized need not be pre-packaged nor pre-sealed prior to its being disposed into the autoclave;

The spout 28 may alternatively be constructed as a bellows, or of telescoping or collapsing members, or of movable skirts, etc., so long as a closed conduit can be effected between the bottom of the shredder and the top of the autoclave;

The autoclave may be mechanically lift up to the spout rather than the bottom of the spout's being lowered to the autoclave;

The gate 29 may be provided above or below the shredder 27;

The autoclave may be stationary and the feed system movable;

Hopper may be fed by an inclined belt conveyor with waste in box or bag form;

Skip hoist may be loaded directly with boxes or bags of waste; or,

Skip hoist may discharge directly into autoclave without being shredded.

Accordingly, the scope of the invention should be determined not by the embodiment illustrated, but by the appended claims and their legal equivalents.

We claim:

1. An apparatus for rendering contaminated material safe for disposal comprising:

(a) a sealable vessel;
said vessel having an interior chamber comprising a substantially cylindrical first side wall member, said chamber having a top and a bottom, and a substantially vertical axis extending between said top and said bottom of said chamber;

(b) means for introducing steam into said vessel;
said means for introducing steam into said vessel comprising a first steam conduit, wherein said first steam conduit extends from the exterior of said vessel into the bottom of said interior chamber;

(c) an aperture in said vessel, said aperture extending from the exterior of said vessel to said top of said interior chamber;

(d) means for retaining said steam inside of said chamber at a pressure greater than 50 psig and at a temperature above 212 degrees Fahrenheit,
said means for retaining said steam comprising means for selectively opening and closing said aperture in said vessel; and (e) a receptacle operationally insertable into said interior chamber of said vessel through said aperture, said receptacle being adapted to contain contaminated solid waste material in bulk;
wherein said receptacle comprises an open-top basket member having a substantially cylindrical second side wall member, said second side wall member demarcating an interior and an exterior of said open-top basket member;
and wherein said second side wall member is porous;

and said second side wall member is permeable to steam;

and wherein said open-top basket member has a finite volumetric capacity defined as the entire volume of said open-top basket member which is interior to said second side wall member of said basket member;

and wherein said open-top basket member is adapted to be bulk-filled to at least 90% of its volumetric capacity with said contaminated solid waste material in bulk; and (f) said open-top basket member further comprising a porous bottom member, said porous bottom member being attached to said second side wall member of said open-top basket member;

wherein said porous bottom member is adapted to contain to said contaminated solid waste material in bulk;

and said porous bottom member of said basket member is permeable to steam; and (g) an annular first plenum between said first side wall member and said second side wall member, said first plenum surrounding said second side wall member and being substantially continuous over the entire length of said cylindrically shaped second side wall member;

(h) a second plenum between said bottom of said chamber and said bottom member of said basket member; and (i) said open-top basket member further comprising a substantially cylindrically-shaped porous inner third wall member having a first end and a second end, the axis of said cylindrically-shaped porous inner third wall member being aligned with said axis of said interior chamber of said vessel;

said inner third wall member being adapted to contain to said contaminated solid waste material in bulk, and permeable to steam;

said inner third wall member being attached at its first end to said porous bottom member of said open-top basket member; and (j) said open-top basket member further comprising an inner third wall top member;

said inner third wall top member being adapted to contain to said contaminated solid waste material in bulk, and said inner third wall top member being attached to said second end of said inner third wall member; and (k) further comprising a second opening in said porous bottom member of said basket member, said second opening in said porous bottom member of said basket member encompassing the axis of said cylindrically-shaped porous inner third wall member; and (l) further comprising a third plenum, wherein said inner third wall member encircles said third plenum.

2. The apparatus according to claim 1, wherein said first steam conduit is perforated and extends vertically through said second opening in said porous bottom member of said basket member.

3. The apparatus according to claim 2, wherein:
said second side wall member of said basket member comprises wire mesh; and
the outside diameter of said second wall member of said basket member is at least 90 percent of the inside diameter of said cylindrical first wall member of said vessel.

4. The apparatus according to claim 3, wherein said wire mesh has a gross opening area of no more than 75% of the total exterior surface area of said second side wall member of said basket member;
and wherein said wire mesh comprises stainless steel wire which is of no greater diameter than Number 12 gauge.

5. The apparatus according to claim 4, wherein:
said contaminated solid waste material comprises fragmented solid waste material; and,
said receptacle member and said contaminated solid waste material in bulk occupy at least 90% of the total volumetric capacity of said interior chamber of said vessel.

6. The apparatus according to claim 5, further comprising:
a hopper member, said hopper member having an interior and an exterior and adapted to receive discrete pre-packaged containers enclosing contaminated solid waste material, said pre-packaged containers enclosing contaminated solid waste material being impermeable to water;
means for sealing said pre-packaged containers enclosing contaminated solid waste material within the interior of said hopper member, said means for sealing said pre-packaged containers enclosing solid waste material within the interior of said hopper member comprising a selectively openable and closeable hatch member;
means, in communication with said hopper member, for shredding said discrete pre-packaged containers enclosing contaminated solid waste material into said contaminated solid waste material in bulk when said hatch member is in a closed position;
and means for transferring said contaminated solid waste material in bulk from said hopper member into said vessel through said aperture in said vessel.

7. The apparatus according to claim 6, further comprising:
means for selectively positioning said vessel beneath said hopper member;
means for removing said receptacle member from said vessel, said means for removing said receptacle member from said vessel comprising a hoist member;
and means for loading said discrete pre-packaged containers enclosing contaminated solid waste material into said hopper member from above said hopper member.

8. An apparatus for rendering contaminated material safe for disposal comprising:
a vessel comprising an interior chamber;
wherein said interior chamber comprises a substantially cylindrical first side wall member, a top and a bottom, and a substantially vertical axis extending between said top and said bottom of said interior chamber;
a closeable aperture in said vessel, said aperture extending from the exterior of said vessel to said top of said interior chamber; closeable vent means extending from said interior chamber to the exterior of said vessel;
a receptacle operationally insertable into said interior chamber of said vessel through said aperture, said receptacle being adapted to contain contaminated solid waste material in bulk;
wherein said receptacle comprises an open-top basket member having a substantially cylindrical second side wall member, said second side wall member demarcating an interior and an exterior of said open-top basket member; and, said second side wall member being porous;

wherein said second side wall member is permeable to steam;

and further comprising means for selectively opening and closing said aperture, said means for selectively opening and closing said aperture comprising a hatch member;

and means for applying heat to said contaminated solid waste material in bulk through openings in said second sidewall member when said hatch member is in a closed position and said closeable vent means is closed;

wherein said means for applying heat to said contaminated solid waste material in bulk through said openings in said second sidewall member comprises means for pressurizing said first interior chamber;

and wherein said means for pressurizing said first interior chamber comprises means for introducing steam into said interior chamber, said steam being at a pressure greater than 50 psig and at a temperature above 212 degrees Fahrenheit;

and wherein said open-top basket member further comprises a porous bottom member, said porous bottom member being attached to said second side wall member of said open-top basket member;

wherein said porous bottom member is adapted to contain to said contaminated solid waste material in bulk;

and said porous bottom member of said basket member is permeable to steam;

and wherein said means for applying heat to said contaminated solid waste material in bulk further comprises an annular first plenum between said first side wall member and said second side wall member, whereby said first plenum surrounds said second side wall member and is substantially continuous over the entire length of said cylindrically shaped second side wall member;

and further comprising a second plenum between said bottom of said chamber and said bottom member of said basket member;

and wherein said open-top basket member has a finite volumetric capacity defined as the entire volume of said open-top basket member which is interior to said second side wall member of said basket member;

and wherein said open-top basket member is adapted to be bulk-filled to at least 90% of its volumetric capacity with said contaminated solid waste material in bulk;

and wherein said means for introducing steam into said vessel comprises a first steam conduit, wherein said first steam conduit extends from the exterior of said vessel into the bottom of said interior chamber;

and wherein said open-top basket member further comprises:

a substantially cylindrically-shaped porous inner third wall member having a first end and a second end, the axis of said cylindrically-shaped porous inner third wall member being aligned with said axis of said interior chamber of said vessel, said inner third wall member being adapted to contain to said contaminated solid waste material in bulk, and permeable to steam, and said inner third wall member being attached at its first end to said porous bottom member of said open-top basket member;

and an inner third wall top member, said inner third wall top member being adapted to contain to said contaminated solid waste material in bulk, and said inner third wall top member being attached to said second end of said inner third wall member;

and further comprising a second opening in said porous bottom member of said basket member, said second opening in said porous bottom member of said basket member encompassing the axis of said cylindrically-shaped porous inner third wall member;

and further comprising a third plenum, wherein said inner third wall member encircles said third plenum.

9. An apparatus for rendering contaminated material safe for disposal comprising:

(a) a sealable vessel;

said vessel having an interior chamber comprising a substantially cylindrical first side wall member, said chamber having a top and a bottom, and a substantially vertical axis extending between said top and said bottom of said chamber;

(b) means for introducing steam into said vessel;

said means for introducing steam into said vessel comprising a first steam conduit, wherein said first steam conduit extends from the exterior of said vessel into said interior chamber;

(c) an aperture in said vessel, said aperture extending from the exterior of said vessel to said top of said interior chamber;

(d) means for retaining said steam inside of said chamber at a temperature above 212 degrees Fahrenheit, said means for retaining said steam comprising means for selectively opening and closing said aperture in said vessel; and (e) a receptacle operationally insertable into said interior chamber of said vessel through said aperture, said receptacle being adapted to contain contaminated solid waste material in bulk;

wherein said receptacle comprises an open-top basket member having a substantially cylindrical porous second side wall member, said second side wall member demarcating an interior and an exterior of said open-top basket member;

and wherein said porous second side wall member is permeable to steam;

and wherein said open-top basket member has a finite volumetric capacity, defined as the entire volume of said open-top basket member which is interior to said second side wall member of said basket member, which is adapted to be bulk-filled with said contaminated solid waste material in bulk; and (f) said open-top basket member further comprising a porous bottom member, said porous bottom member being attached to said second side wall member of said open-top basket member, and said porous bottom member of said basket member being permeable to steam; and (g) an annular first plenum between said first side wall member and said second side wall member, said first plenum surrounding said second side wall member and being substantially continuous over the entire length of said cylindrically shaped second side wall member;

(h) a second plenum between said bottom of said chamber and said bottom member of said basket member; and (i) said open-top basket member further comprising a substantially cylindrically-shaped porous inner third wall member having a first end and a second end, the axis of said cylindrically-shaped porous inner third wall member being substantially parallel to said axis of said interior chamber of said vessel;

said inner third wall member being adapted to contain to said contaminated solid waste material in bulk, and permeable to steam;

said inner third wall member being attached at its first end to said porous bottom member of said open-top basket member; and (j) said open-top basket member further comprising an inner third wall top member;

said inner third wall top member being adapted to contain to said contaminated solid waste material in bulk, and said inner third wall top member being attached to said second end of said inner third wall member; and (k) further comprising a third plenum, wherein said inner third wall member encircles said third plenum.

* * * * *